US00PP12635P2

(12) United States Plant Patent
Booman

(10) Patent No.: US PP12,635 P2
(45) Date of Patent: May 21, 2002

(54) BEGONIA PLANT NAMED 'MINI MIAMI'

(76) Inventor: James Lawrence Booman, 2302 Bautista Ave., Vista, CA (US) 92084

( * ) Notice: Subject to any disclaimer, the term of this patent is extended or adjusted under 35 U.S.C. 154(b) by 0 days.

(21) Appl. No.: 09/624,467

(22) Filed: Jul. 24, 2000

(51) Int. Cl.[7] ..... A01H 5/00
(52) U.S. Cl. ..... Plt./343

(58) Field of Search ..... Plt./343

*Primary Examiner*—Bruce R. Campell
*Assistant Examiner*—Anne Marie Grünberg
(74) *Attorney, Agent, or Firm*—C. A. Whealey

(57) ABSTRACT

A new and distinct cultivar of Begonia plant named 'Mini Miami' characterized by its dense, uniform, outwardly arching and dwarf plant habit; rapid plant growth; bright silvery leaves blushed with bright to hot pink with dark purple brown centers; and serrate leaf margin.

1 Drawing Sheet

BACKGROUND OF THE INVENTION

The present Invention relates to a new and distinct cultivar of Begonia, botanically known as *Begonia rex* hybrid, commercially known as Rex Begonia, and hereinafter referred to by the cultivar name 'Mini Miami'.

The new Begonia was discovered by the Inventor in a controlled environment in Vista, Calif., as a naturally-occurring mutation of the *Begonia rex* hybrid cultivar Mini Merry Christmas, not patented. The new Rex Begonia was observed as a single plant in a group of plants of the parent cultivar. The selection of this plant was based on its unique leaf coloration and pattern.

Asexual reproduction of the new Begonia by leaf cuttings taken in a controlled environment in Vista, Calif., has shown that the unique features of this new Begonia are stable and reproduced true to type in successive generations.

SUMMARY OF THE INVENTION

The new Begonia has not been observed under all possible environmental conditions. The phenotype may vary somewhat with variations in environment such as temperature, daylength, light intensity, nutritional and water status without, however, any variance in genotype.

The following traits have been repeatedly observed and are determined to be the unique characteristics of 'Mini Miami'. These characteristics in combination distinguish 'Mini Miami' as a new and distinct cultivar:

1. Dense, uniform, outwardly arching and dwarf plant habit.
2. Rapid plant growth.
3. Does not require winter dormancy.
4. Bright silvery leaves blushed with bright to hot pink with dark purple brown centers; under high light conditions and good fertility, leaf color becomes almost red.
5. Serrate leaf margin.

BRIEF DESCRIPTION OF THE PHOTOGRAPH

The accompanying colored photograph illustrates the overall appearance of the new Begonia. This photograph shows the colors as true as it is reasonably possible to obtain in colored reproductions of this type. Colors in the photograph may differ slightly from the color values cited in the detailed botanical description, which more accurately describe the actual colors of the new Begonia. The photograph comprises a side perspective view of a typical plant of 'Mini Miami'.

DETAILED BOTANICAL DESCRIPTION

The aforementioned and following observations, measurements and values describe plants grown in a polyethylene-covered greenhouse in Lompoc, Calif., during the spring under conditions which approximate commercial production practices. After the cuttings were rooted, plants were planted in 10-cm containers and grown with day temperatures ranging from 27 to 32° C., night temperatures ranging from 18 to 20° C., and light levels about 1,800 foot-candles. Plants used for the description were about 6 to 8 weeks old. In the following description, color references are made to The Royal Horticultural Society Colour Chart except where general terms of ordinary dictionary significance are used.

Botanical classification: *Begonia rex* hybrid cultivar Mini Miami.

Parentage: Naturally-occurring mutation of *Begonia rex* hybrid cultivar Mini Merry Christmas, not patented.

Propagation:

*Type.*—By leaf cuttings.

*Time to initiate roots.*—About 21 days at 21° C.

*Time to develop roots.*—About 56 days at 21° C.

*Rooting habit.*—Numerous, fine, fibrous, freely branching.

Plant description:

*Plant form.*—Rosette; dwarf; full and dense; uniform; outwardly arching potted plant; freely basal branching with good leaf petiole strength.

*Growth habit.*—Rapid growth rate; moderately vigorous. Suitable for 10-cm containers.

*Crop time.*—To produce a 10-cm container flowering plant, about 6 to 8 weeks are required after planting a rooted leaf cutting.

*Branching habit.*—Very freely basal branching with about 15 to 20 leaves per plant.

*Plant height, soil level to top of flowers.*—About 15 cm.

*Plant width.*—About 17 cm.

Foliage description:

*Length.*—Petiole to apex: About 5.3 cm. Base to apex: About 6.7 cm.

*Width.*—About 4.8 cm.

*Shape.*—Asymmetrical, oblique, roughly ovate.

*Apex.*—Sharply acute.

*Base.*—Asymmetrically cordate, not equilateral.

*Margin.*—Serrate with fine ciliation.

*Texture.*—Leathery, rugose; pubescence on lower surface veins.

*Color.*—Upper surface: Margin, purple to brown, 187A to 200A; central veinal area, 187A; central veinal area surrounded by 60A to 184B overlain with close to 187A to 191B; intermarginal, 191B; veins, 187A; iridescent. Lower surface: Margin, 187A; central veinal area, 187A; intermarginal, close to 191B.

*Petiole.*—Length: About 4.6 cm. Diameter: About 3 mm. Shape: Longitudinally channeled. Texture: Pubescent. Color: 183A to 187A.

*Stipules.*—Length: About 1.2 cm. Diameter, base: About 6 mm. Shape: Deltoid. Color: Close to 183B.

Flower description: Flower development has not been observed.

Disease resistance: Plants of the new Rex Begonia have been noted to be more resistant to Powdery Mildew than large-leaf Rex Begonias known to the Inventor.

Temperature tolerance: Plants of the new Rex Begonia tolerate temperatures ranging from 0° to 46° C.

It is claimed:

1. A new and distinct Begonia plant named 'Mini Miami' as illustrated and described.

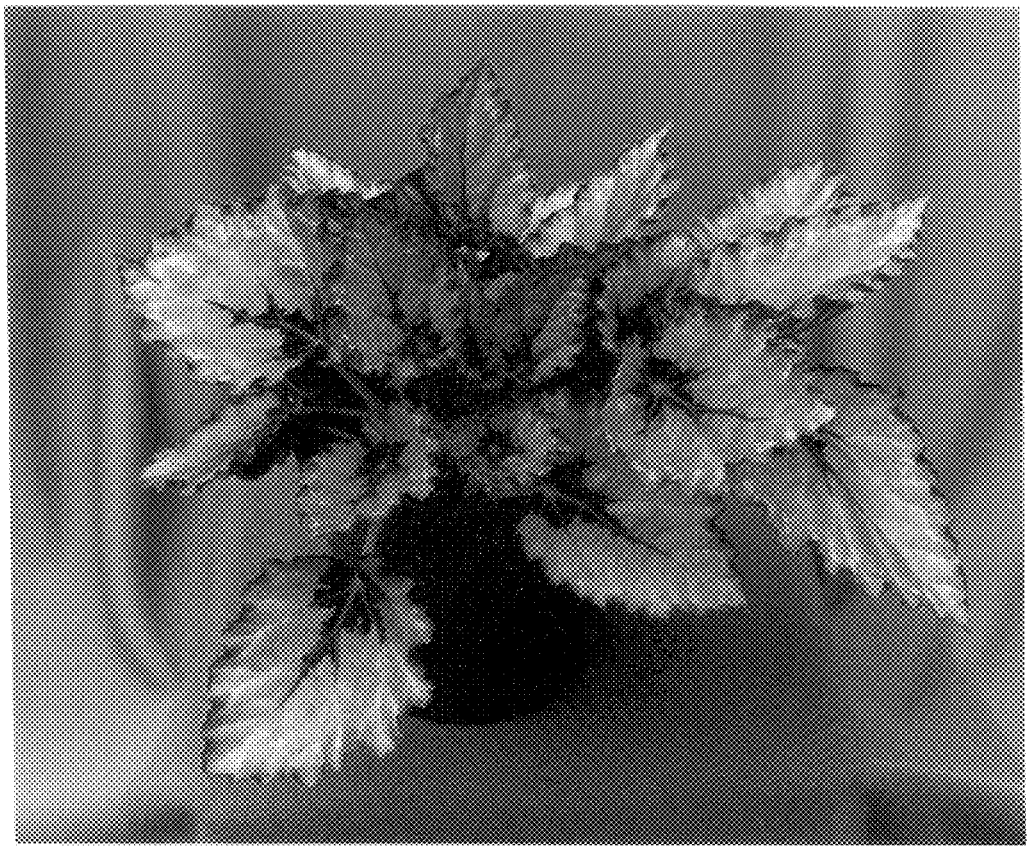

* * * * *